United States Patent [19]

Malmros et al.

[11] Patent Number: 4,916,075
[45] Date of Patent: Apr. 10, 1990

[54] DIFFERENTIAL HOMOGENEOUS IMMUNOSENSOR DEVICE

[75] Inventors: Mark K. Malmros, Newton; Julian Gulbinski, III, Jamison, both of Pa.

[73] Assignee: Ohmicron Corporation, Del.

[21] Appl. No.: 87,087

[22] Filed: Aug. 19, 1987

[51] Int. Cl.⁴ .......................... C12M 1/00; C12M 1/40
[52] U.S. Cl. ..................................... 435/291; 204/403; 324/71.5; 422/82.01; 435/7; 435/288; 435/817; 436/528; 436/531; 436/532
[58] Field of Search ............... 436/528, 531, 532, 151, 436/; 422/68; 435/7, 817, 291, 288; 324/71.5, 450, ; 204/403

[56] References Cited

U.S. PATENT DOCUMENTS

| | | | |
|---|---|---|---|
| 4,334,880 | 6/1982 | Malmros | 435/291 X |
| 4,444,892 | 4/1984 | Malmros | 436/528 |
| 4,839,017 | 6/1989 | Taniguchi et al. | 204/403 |

Primary Examiner—G. L. Kaplan
Attorney, Agent, or Firm—Omri M. Behr

[57] ABSTRACT

There is provided a novel method of testing for the presence of an analyte in a fluid suspected of containing the same. In this method, in the presence of the analyte, a substance capable of modifying certain characteristics of the substrate is bound to the substrate and the change in these qualities is measured.

While the method may be modified for carrying out quantitative differential analyses, it eliminates the need for washing analyte from the substrate which is characteristic of prior art methods.

8 Claims, 10 Drawing Sheets

SAMPLE

REFERENCE

DIFFERENTIAL HOMOGENEOUS IMMUNOSENSOR DEVICE

A portion of the work disclosed in the present application was made pursuant to Department of Energy contract DE-AC-01-84-ER-80173. The Government may have rights herein.

BACKGROUND OF THE INVENTION

Many testing methods are known to test for small quantities of analyte in fluids, particularly body fluids. Many of these tests depend upon basic principals of immune reactions namely, that an antigen will bind with an antibody having a specific or general affinity therefore. It is well known to bind such antibodies to other agents or passive carriers to which may be linked certain detectable agents, thus enabling readily detectable responses to be obtained from the presence of exceedingly small quantities of the analyte sought. Well known among such tests are hemagglutination tests and the ELISA test.

The basic problems with the tests of the prior art are two-fold. They either require the running of comparative blank tests on separate samples of substrate and/or they require multiple operations including the washing of the test substrate to remove therefrom unreacted reagents and reactants.

Heretofore, it has not been possible to provide a system wherein the reactants and reagents are loaded together into a single test cell or container and qualitative or quantitative measurements made with the substances still in situ, without the need for separate blanks or washing of the cell prior to making the measurement.

SUMMARY OF THE INVENTION

It has been found that when an agent capable of modifying measurable and/or detectable qualities of a substrate is bound to the substrate and said activating mechanism caused to operate, the modifying agent will preferentially affect the substrate rather than the surrounding solution. This principle is the basis of the several embodiments of the detection system disclosed and claimed herein.

The modification of the electrical properties, i.e., resistivity or conductivity of certain conductive or semiconductive polymers by the doping thereof with certain dopants is well known. Thus, the preferential introduction of a dopant into such a polymer by means of a dopant generating component linked to the polymer, constitutes the operating principle of one embodiment of the present invention.

The sensors utilized in the main embodiment of the present invention comprise a substrate, suitably a film of semiconductive polymer, having an obverse and a reverse surface. On the reverse surface and in contact therewith, there is provided a common electroconductive area and at least one further electroconductive area similarly in contact with the reverse side. Since most applications of this invention would be directed to at least the qualitative determination of the presence of an analyte, or indeed, quantitative measurement, it is preferred to provide a second further electroconductive area at a different location on the reverse side. There is further provided, to the observe side of the film, a means of dividing the obverse side in such a way that the portion of the film carrying the first further electroconductive area and a portion of the common electroconductive area lie on one side of said separating means and the other second further electroconductive area and the remaining portion lie on the other side. As will appear herein below, this separating means need not be a permanent separating means.

In the general mode of operation of the system a binding agent for the analyte is bound directly or indirectly to the substrate. A fluid suspected of containing the analyte is caused to contact the substrate carrying the binding agent and immediately thereafter, there is added a substrate modifying agent, comprising at least one first component bound to a further portion of a binding agent which, either has an affinity for the analyte or competes with the analyte with respect to binding to the binding agent upon the substrate, and at least one second component reactable with said first component to generate a factor capable of modifying the modifiable quantity of the substrate. It is advantageous to further provide a scavenger for said modifying factor.

It is preferred to operate the system of the present invention in an immunoassay cell comprising the sensor described above. In this cell electrical connection means are provided to the electroconductive areas. A sample reservoir having an upper and lower end is placed with its lower end in contact with the obverse surface of the sensor film in such a manner that the contact between said lower end and said film is liquid leak proof and the open area is large enough to encompass all or most of the obverse surface lying over the electroconductive areas on the reverse side.

There is also provided a dual chamber insert adapted to fit removeably inside the reservoir. This insert is provided with a dividing part or center partition which, when in place, would constitute the means for separating the first field from the second field of the obverse side of the film. The center partition and the lower edge of the insert chamber are adapted to contact the obverse surface of film again in a leak proof manner. In the operation of the system, into one chamber designated the sample side, is inserted a solution containing a binding agent and any other such substances required to bind said binding agent to substrate. Into the other chamber designated the reference side, there is either inserted no solution or a solution containing whatever other substances are to be bound to said reference side. Upon completion of the binding step the solutions are poured out of the cell. If desired, the two chambers can be washed out but this is not strictly necessary and the dual chamber insert removed.

There is then introduced into the reservoir or sample well, the analyte and the solution containing the substrate modifying agent. Since the first components of the substrate modifying agent will usually react quite rapidly with the second component, it is advisable to add all three components in succession, the order of addition however, not being important. Desirably, there is also added the scavenger for the modifying factor.

The first component will then react with the second component whereby the modifying factor is generated. If the circumstances of the assay are such that the first component is bound to the substrate, the modifying factor will preferentially pass to the substrate modifying its modifiable quality. In the case of a electroconductive polymer, this being its conductivity or resistivity, which then can be measured. That portion of the modifying factor generated by the first component which is not bound by the substrate will pass into the solution and be scavenged by the scavenger.

DESCRIPTION OF THE PREFERRED EMBODIMENTS

While the principles of the present invention are not limited thereto, it is preferred to carry out the present invention by measuring the changes in conductivity or resistivity of conductive or semi-conductive polymers. Among the polymers which may be utilized in this invention there may be mentioned a polyacetylene, polypyrrole, polyparaphenylene, polythiophene, and polysulfone. This is not intended to be a limitation, especially preferred however, is polyacetylene.

The polymers may be films or compressed powder composites. They may be utilized as single component conductive or semiconductive material mixtures within the class or, composites or blends with nonconductive polymers such as polyethylene or polystyrene. Blends, wherein the polyacetylene is formed in or on a nonconductive substrate have been found useful.

These substrates may be initially doped or undoped. It is preferred to utilize them in the doped form. Dopants which may be utilized include: Among the preferred dopants especially when polyacetylene is utilized, is iodine.

The sensors, suitably containing polyacetylene, utilized in the present invention may be prepared in accordance with the procedures set forth in U.S. Pat. No. 4,444,892, or preferably U.S. Pat. No. 4,394,304 the disclosure of which is incorporated herein by reference. The dopant is introduced to provide a nominal resistance of between 0.001 and 100 megohms preferably between 0.1 and 10 megohms, most suitably, about 1 megohm per centimeter. The doping is carried out by dissolving the requisite amount of iodine in a non-polar low molecular weight organic solvent, suitably a lower alkane such as hexane, immersing the film therein for between 4 and 16 hours, rinsing the film in solvent and drying under reduced pressure. In order to provide the electroconductive areas to the reverse side of the film, a thick film of hybrid electrode pattern is applied by spraying, or screening through a mask, an electroconductive material, suitably colloidal graphite paint.

Figure 1:
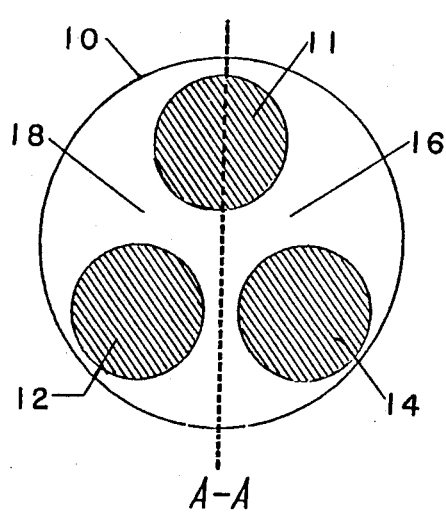
FIG. 1 shows the downward plan view upon the obverse side of a sensor of the present invention.

In one embodiment of the present invention, as illustrated in FIG. 1, there is provided a disk 10 of electroconductive material, suitably of a polyacetylene blend, suitably doped with a predetermined amount of iodine. Three predetermined electroconductive areas 11, 12 and 14, are provided on the reverse side of the disk. It is preferred, but not critical, that area 11 lie on a diameter, suitably close to but not at the outer circumference of the disk. Areas 16 and 18 are so provided that at least part of both areas lie over electroconductive area 11 and, suitably the entire of electroconductive area 14 lies under segment 16 and electroconductive area 12 lies under segment 18. It is preferred, though not essential, that electroconductive areas 12 and 14 lie on opposite sides of a diameter passing through area 11 and that areas 12 and 14 are substantially equidistant from area 11.

In a modification of the device shown in FIG. 2, there is again provided a disk 101. Again, the electroconductive areas are provided to the reverse of the disk. A central conductive area 111 is provided along the entire diameter BB having edges on either side of said diameter BB, spaced apart therefrom. The two other electroconductive areas 112 and 114, are provided in the space between chords 113 and 115, suitably but not critically equidistant from axis BB and parallel thereto, and the circumference of the disk. There are thus provided two uncoated areas on the obverse side, 116 and 118, lying between the common electrode and the outer electroconductive areas.

Figure 2:
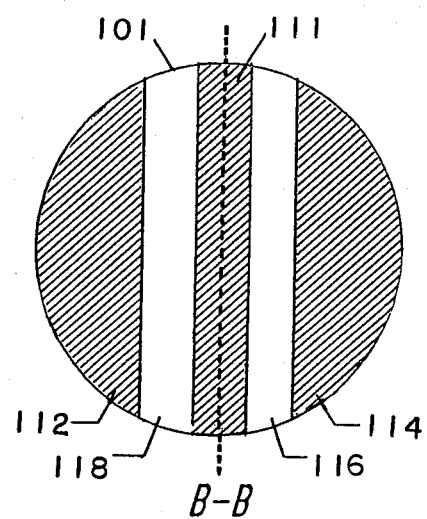
FIG. 2 is a downward plan view upon the obverse side of a further embodiment of a sensor of the present invention.
Figure 3:
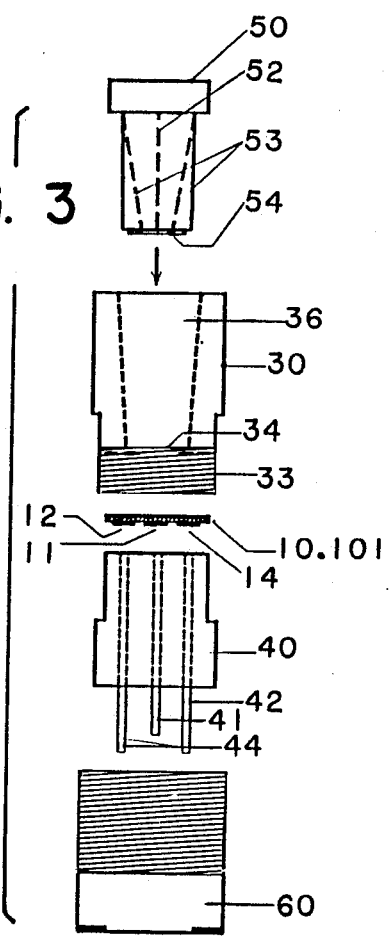
FIG. 3 is an exploded cross-sectional elevational view of an electrode cell of present invention.
Figure 4:
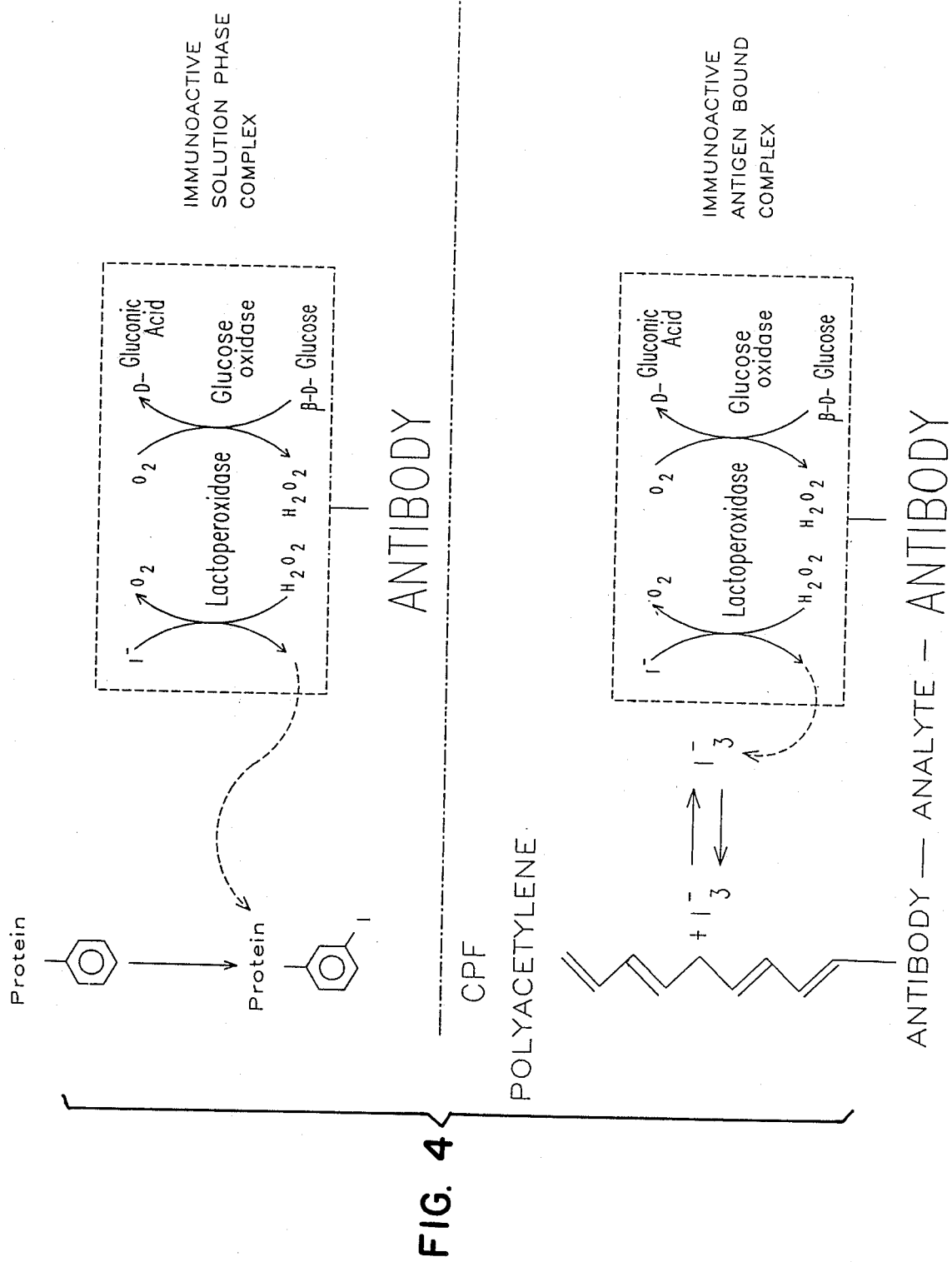
FIG. 4 is an illustration of the solution phase, complex and the surface confined complex of the interactions between the components of the substrate modifying agents, the scavenger, and the substrate in one embodiment of the invention.

FIG. 3 illustrates a sensor of FIG. 1 or FIG. 2 in its operating environment, that is to say, an immunoassay sensor cell. In this cell, there is provided a base assembly 40 having contact means 41, 42 and 44, mounted therein, the upper ends of said contact means being electrically contactable with electroconductive areas on the reverse side of the sensor disk and the other ends thereof being formed, suitably, as electrode pins and insertable into a base retention means 60. There is provided a sample well 30 having a reservoir 36 therein and a lower end 34 adapted to contact and form a liquid, leak-proof seal with the obverse surface of the sensor. The opening in lower end 34 is of sufficient size to encompass at least a portion, suitably a major portion of the obverse surface above the electroconductive means on the reverse side of the disk. Suitably, a screw thread 33 is provided on the outside of the lower portion of sample well 30, sized to interact with a similar screw thread on base retention unit 60, so that when the base assembly 40 is inserted into base retention unit 60, sensor 1 (or 101) placed on said base assembly 40 and sample well 30, placed upon said sensor and screwed into base retention unit 60, the aforesaid leak-proof seal and electrical contacts are secured.

There is further provided a dual insert chamber 50 having baffles 53 set on the inner surface of the chamber and a center partition 52 provided across an internal diameter thereof. Bottom edge 54 of chamber 50 is provided to contact the upper surface of sensor 1 (or 101) in a leak-proof manner. Furthermore, center partition 52 is of sufficient length and has a lower edge which, when the dual chamber insert is inserted into the sample well and a liquid placed on one side of the partition, the liquid will not leak to the other side of the partition across the surface of the sensor. In the operation of the first stage of the device, the center partition is so oriented as to lie on diameters AA or BB on the sensor.

In the operation of the cell, the operating areas, that is to say, areas 18, 118, 16 and 116, are treated to provide different immune reactions. Thus, one area, suitably 16, 116, becomes designated as the sample area. In the preparation of the stage of the device, a binding agent specific to the analyte is poured into that portion of the dual insert chamber overlying area 16, 116. It is usually not necessary to pre-prepare the surface of the sensor. A sufficient binding to the surface thereof will occur by merely contacting the said obverse surface of the sensor with an aqueous solution of the binding agent.

After a suitable contact time, the binding agent is poured out from the dual insert chamber, the treated segment, suitably, washed with water, and the dual insert chamber removed. The cell is then ready for use in accordance with any of the analytical formats and protocols which are set forth in FIG. 5 and which are discussed in detail hereinbelow. It will be clear to one skilled in the art that these formats and protocols are merely the most usual modes of carrying out such an analysis. Other modes may well become apparent to those skilled in the art and are to be included within the scope of the present invention.

It has been found convenient to utilize, as the substrate modifying agent, a first component comprising the combination of lactoperoxidase (LPO) with glucose oxidase (GOX). In the presence of an aqueous solution of glucose (GLU), glucose oxidase generates hydrogen peroxide which in turn causes lactoperoxidase to generate the iodonium or $I^{3-}$ ion. This ion is capable of substantially modifying the conductivity of the polymeric substrate.

In order to illustrate the operation of the device and analytical systems associated therewith, the LPO/GOX/GLU system is discussed. Such discussion is not intended to limit the invention thereto. Other systems may be employed, some of which are mentioned herein, others which will be apparent to those skilled in the art.

Nevertheless, it has been found that the LPO/GOX/GLU system has wide applicability as a modifying factor generating system and thus useful as such in a wide variety of tests and test protocols.

Figure 5A:
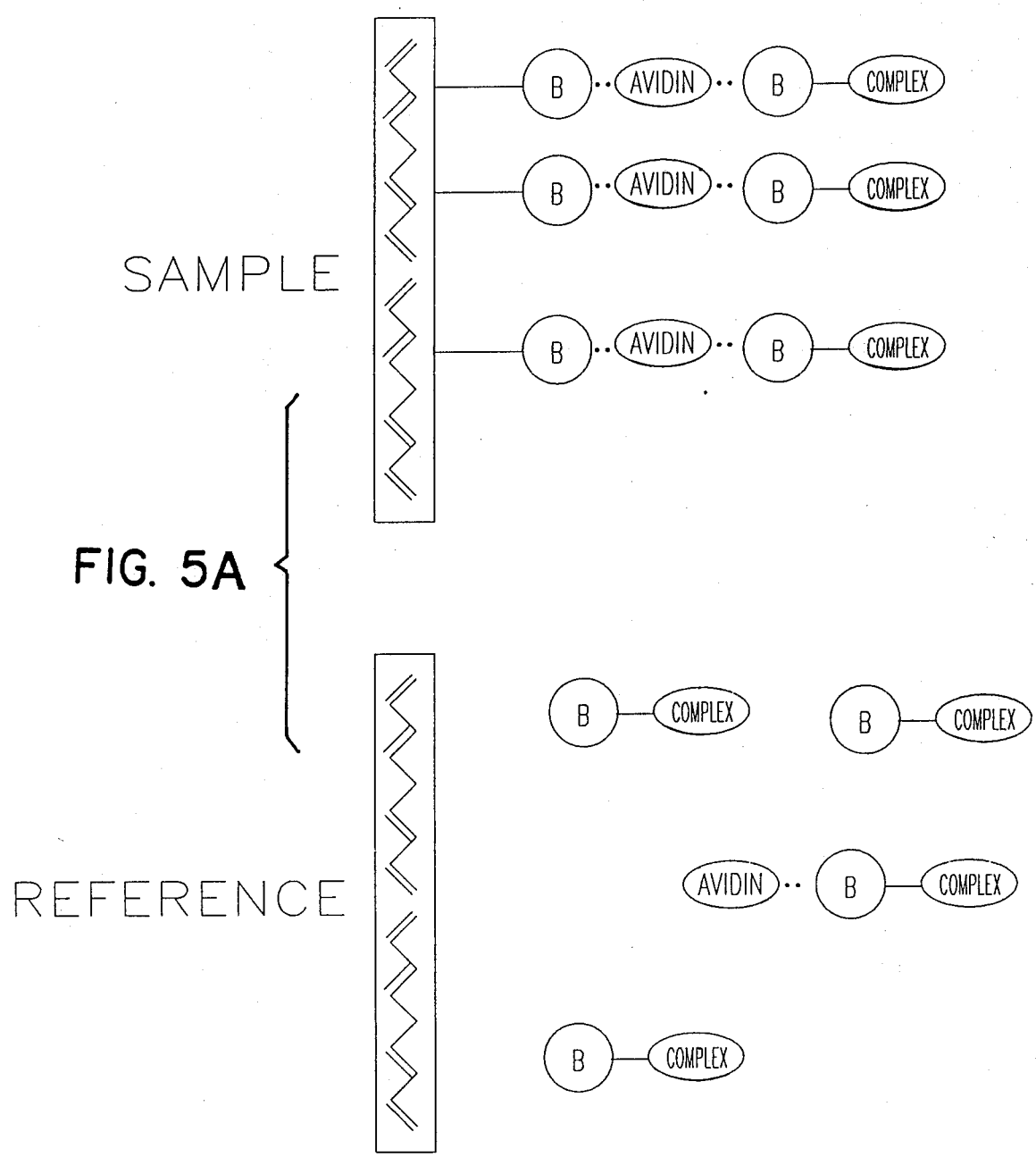
FIGS. 5(a) thru (e) constitute schematic diagrams showing the operation of the same substrate modifying agent illustrated in FIG. 4 as applied to three different assays, two of which are illustrated in two modes (a & b, c & d).

In the modification illustrated in FIG. 5a, known as the sandwich assay, the predetermined binding agent, (for example biotin), is bound to the sample surface 16 116 of the sensor. A further portion of binding agent (B) is bound to the LPO-GOX combination (shown as COMPLEX in the Figure). The reaction components, that is to say, analyte containing sample, a solution of B-LPO-GOX, GLU, and a scavenger for $I^{3-}$, i.e., bovine serum albumin (BSA) are introduced into the sample reservoir 36. The order of introduction is not important. For purposes of this discussion, it is presumed that the analyte itself has more than one binding site and is able to bind to the binding agent B. Thus, if the binding agent B is biotin and the analyte is avidin, as illustrated in the upper (sample) segment of FIG. 5a, biotin is bound both to the substrate and to the LPO (in the COMPLEX). Avidin thus reacts with the substrate-bound biotin and the LPO-bound biotin. The GLU reacting with the GOX generates peroxide, which in turn causes LPO to generate $I^{3-}$ which, by virtue of the binding to the substrate through the analyte, is preferentially caused to be absorbed by the substrate itself. Needless to say, not all of the $I^{3-}$ is thus absorbed. The unabsorbed $I^{3-}$ reacts with the scavenger and is taken out of operation.

In contrast thereto, on the reference side of the cell 18 (118), there is no biotin bound to the surface. Thus, the $I^{3-}$ generated by the LPO remains in solution where it is scavenged by the BSA and does not affect the conductivity of the substrate of the reference segment.

It has been found that the modifying effect discussed hereinabove, can be amplified by (not illustrated) additionally absorbing a certain amount of LPO on the operating substrate itself. Thus, when the GOX generates the peroxide, it will affect the LPO and increases the base line reading. Needless to say, the LPO has to be bound to both the sample 16, 116 and the reference 18, 118 areas.

Figure 5B:
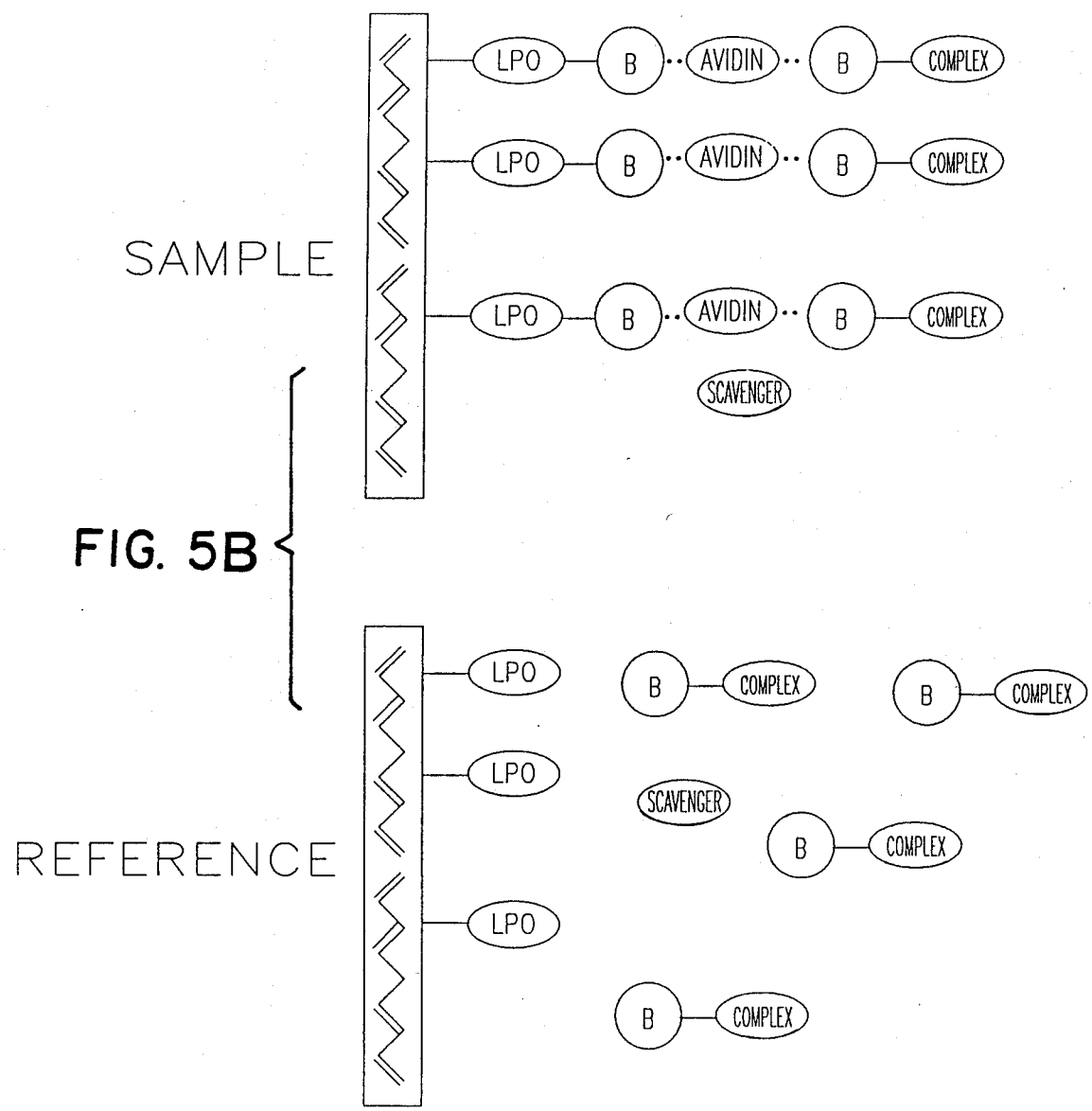

A further modification of this approach is found in the reverse sandwich which is illustrated in FIG. 5b. In this modification, LPO is bound to both the reference and the working surfaces but to the LPO on the working surface is additionally bound the binding agent B. The operation of the device is similar to that of the sandwich device. In the assay, the analyte is bound both to the binding agent on the surface bound LPO and to the binding agent on the "floating", in solution, LPO-GOX. Thus again, the $I^{-3}$ which is generated by action of the LPO on the peroxide will give rise to higher levels on the sample side where the B-LPO-GOX combination is bound through the analyte to the LPO-binding agent combination on the substrate than on the reference side where merely LPO is bound to the substrate.

Figure 5C:
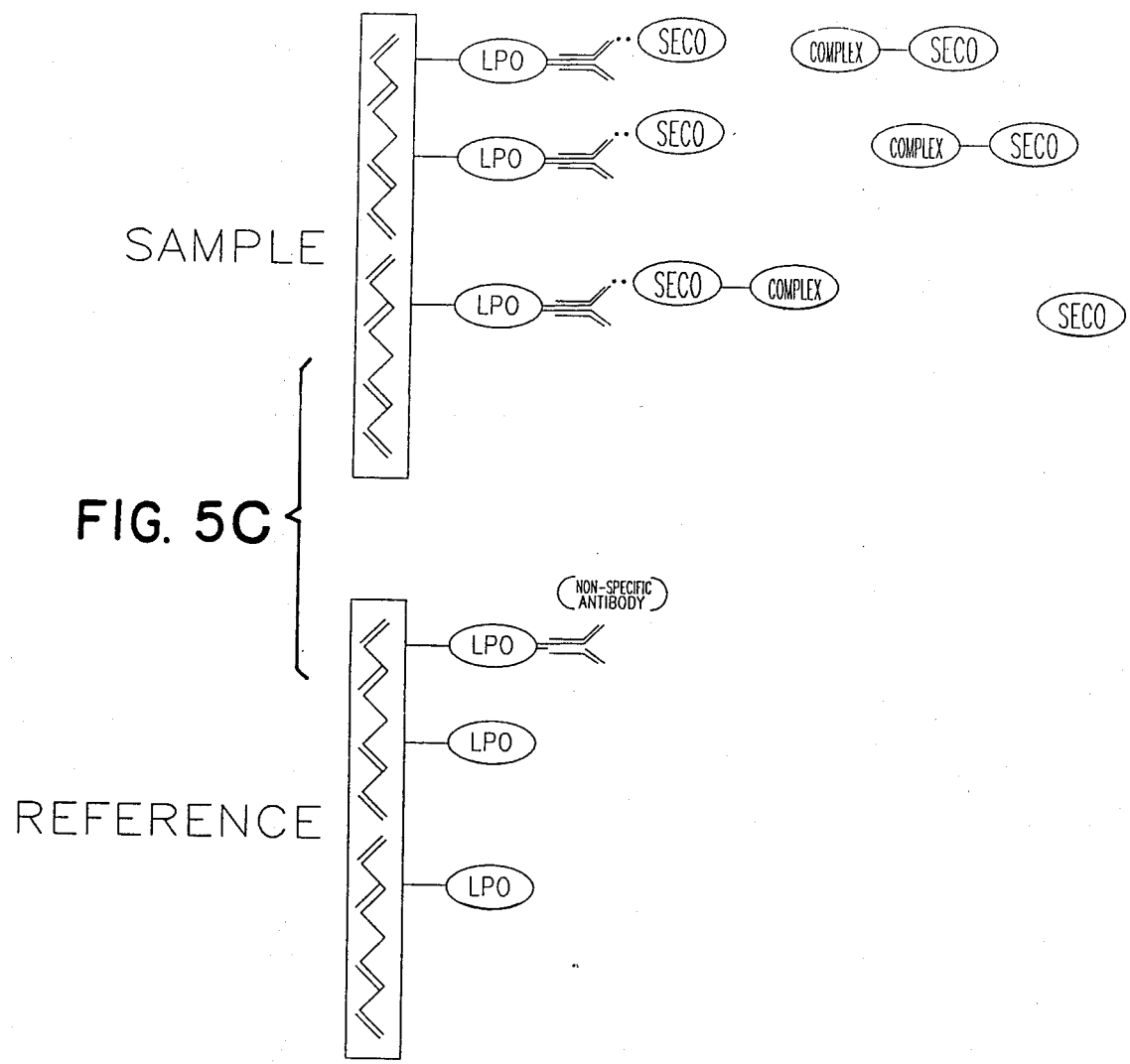

FIG. 5c illustrates one embodiment of the so-called competitive mode which is here illustrated by a procedure utilized to test for the presence of the drug Secobarbital (SECO). In this embodiment, an antibody specific to SECO is bound to the sample substrate area 16, 116 and a non-specific antibody is bound to the reference substrate area 18, 118. To the reference cell 36 are added sequentially a solution suspected to contain the analyte SECO and solutions containing SECO bound to GOX-LPO. In the operation of the device, both the analyte SECO and the LPO-GOX-SECO will compete for reaction with the SECO specific antibody. On the other hand, the non-specific antigen on the reference side, will generally not react with anything. It will thus be seen following the general binding reactions shown in FIGS. 5a and 5B, that the amount of modification on the sample side will be reduced in proportion to an increasing amount of analyte. Again, if desired, the basic signal can be amplified by placing LPO bound to specific anti-SECO antigen on the sample side and LPO bound to the non-specific antigen on the reference side.

Another modification of the competitive homogeneous assay can be operated in the following manner, as shown is FIG. 5d.

On the sample side 16, 116 is placed, as before, a specific anti-SECO antigen. On the reference side is placed a general binder such as avidin. With the analyte containing sample is charged an equal mixture of SECO-GOX-LPO and biotin-GOX-LPO. Thus, if no SECO is present, the SECO-GOX-LPO will bind to anti-SECO and the biotin-GOX-LPO will bind to the avidin, giving rise to a null reading. On the other hand, if SECO is present and completes with SECO-GOX-LPO for the anti-SECO agent, the modification on the working side will be reduced.

Again, the signal level may be amplified by placing on the sample side LPO bound to specific anti-SECO and on the reference side, LPO bound to avidin.

Figure 5D:
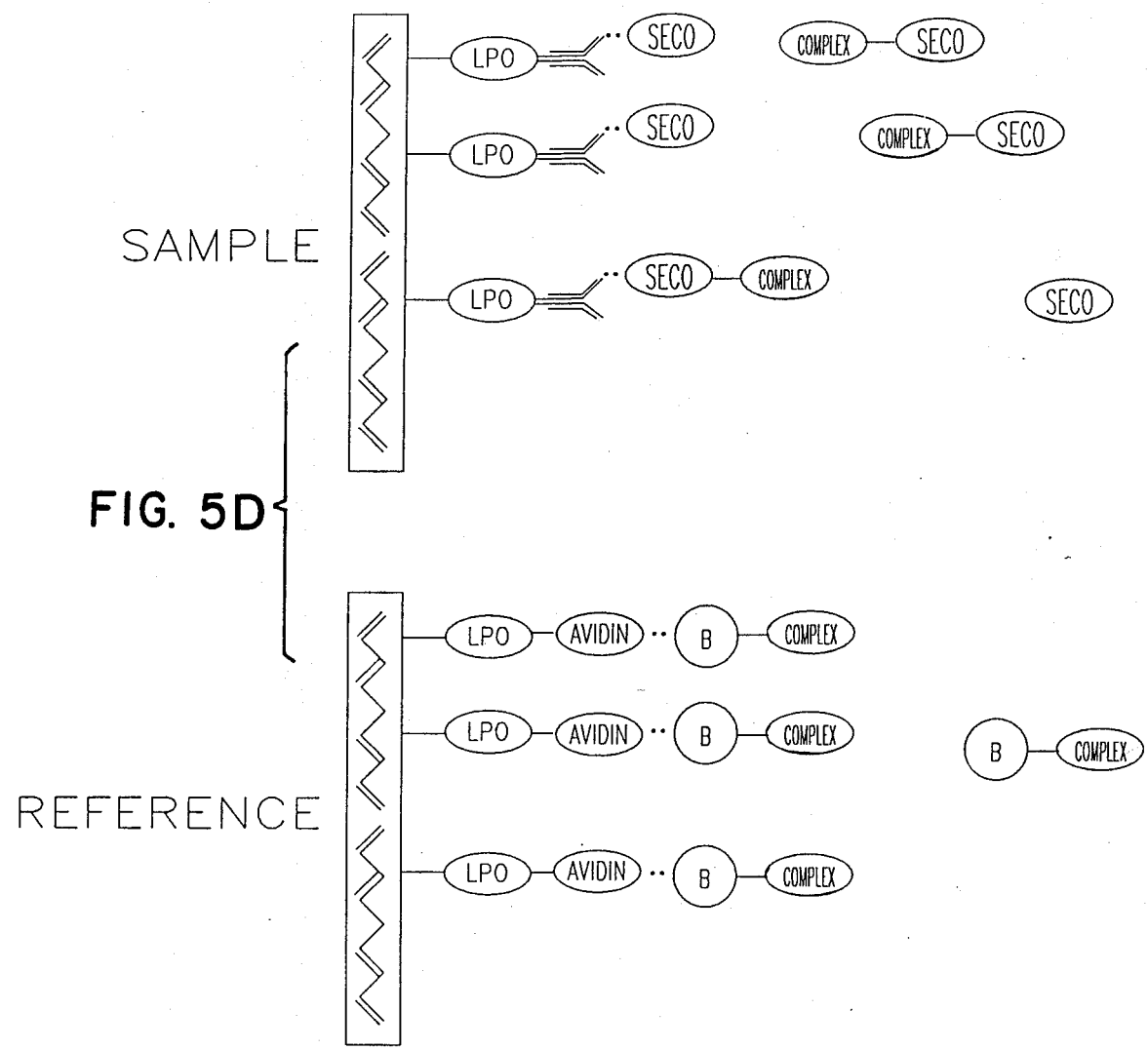
Figure 5E:
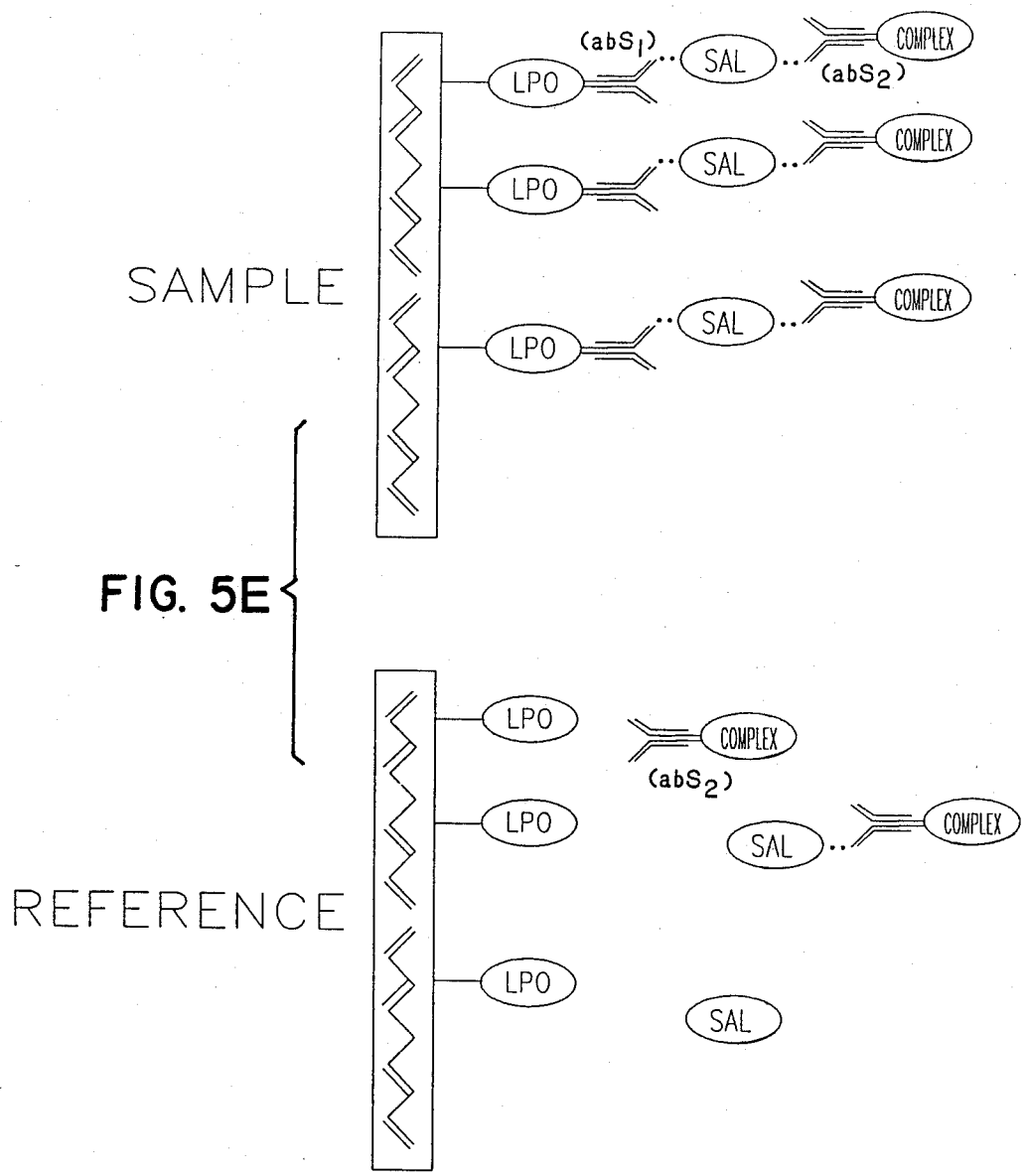

Yet another embodiment is a so-called homogeneous sandwich, which is illustrated in FIG. 5e. This assay may be used for the detection of analytes having at least two different and specifically identifiable binding sites.

It may be used for the detection of peptide containing materials such as proteins. Suitably Salmonella (S) toxin may be detached and monitored by this approach. It depends upon the use of two different but specific antibodies sites $S^1$ and $S^2$ on the analyte. Thus, the sample surface 16, 116 is coated with 100-anti-$S^1$ antibody and anti-$S^2$ antibody is bound to the GOX-LPO. Similarly, the reference side 18 118 is provided LPO bound to a non-specific antiprotein antibody. The anti-$S^2$-GOX-LPO and the solution suspected to contain analytes are then charged to the cell (together with glucose and scavenger). If the analyte actually contains S, then S will bind to anti-$S^1$ and anti-$S^2$ will bind to S on the sample side, thus binding the GOX-LPO modifying factor generating system to the sample side and thus modifying the conductivity on that side. Since there is nothing for the anti-$S^2$ to bind to on the reference side, there will be no modification on the reference side.

Again, similarly anti-$S^1$ antibody itself can be bound to the working side and a non-specific antibody on the reference side.

EXAMPLE I

Preparation of Polyacetylene Films (a) Solvent blend-Kraton

Polyacetylene/Kraton blend is prepared by the polymerization of acetylene gas using a heterogeneous Ziegler-Natta catalyst. The catalyst solution is prepared as a four component system comprising two active components, an inert component, and a solvent. The solution is prepared in a controlled atmosphere (nitrogen) glove box to comprise the active components triethylaluminum A1 ($C_2H_5$) (Ethyl Corporation) and titanium tetrabutoxide (Ti(n $OBu)_4$ (Alfa Products) mixed in a 4:1 mole ratio to a nominal concentration of 200 mM with respect to aluminum. The third component is polystyrene-poly-isoprene-polystyrene triblock polymer, (Kraton, 1107 manufactured by Shell Chemical), which is previously dissolved in the solvent at 10 weight %. The fourth component or solvent used is anhydrous, distilled toluene.

To prepare a sheet of polyacetylene blend film, approximately 20 ml of the catalyst solution is poured into a 110 mm diameter × 50 mm high culture dish (reaction chamber) and the dish clamped between two 5" square sheets of ⅜" thick G10 fiberglass reinforced epoxy composite boards. The upper board is fitted with a rubber gasket which mates with the rim of the dish to thereby create a vacuum tight seal. This upper board is also fitted with gas inlet and outlet ports, a pressure gauge, and a thermistor. The lower board is fitted with a Peltier stage which acts to cool the dish and its contents. Standard welder's acetylene is purified by first bubbling the gas through distilled water or concentrated sulphuric acid to remove traces of acetone, then dried by passing the gas over a column of anhydrous calcium chloride, anhydrous calcium sulphate (Drierite), or phosphorous pentoxide followed by 2A molecular sieves. The purified gas is introduced into the previously evacuated reaction chamber via the inlet port at pressures which vary during synthesis from a few cmHg up to 86 cmHg.

A cohesive film of polyacetylene blend begins growth on the quiescent catalyst solution within a few seconds following entry of the gas. Film growth may be controlled by the judicious selection of time, temperature and gas pressure.

The resulting film is readily removed from the catalyst surface and rinsed repeatedly in anhydrous, distilled toluene until the solvent is clear of the residual dark brown catalyst. The polyacetylene blend films synthesized in this way have a lustrous appearance, are flexible, and mechanically tough. The material is a blend of polyacetylene and kraton with film thicknesses varying from 0.05 to 0.5 mm depending upon the conditions of time, temperature, gas pressure, and catalyst composition employed.

(b) Impregnation - Polyethylene

A 0.3 mm thick commercial low density polyethylene (LDPE) film was soaked in dry toluene for 24 hours to remove additives and immersed in a freshly-prepared solution containing dry toluene (60 ml), $Ti(OBu)_4$ (3.75 ml) and $Et_3$A1 (6 ml) in a Schlenk tube under argon. The tube was heated to ca. 70° C. under a slow stream of argon for ca. 1.5 hr. to impregnate the film with the catalyst. After cooling to room temperature, the catalyst solution was removed with a syringe and the organge-brown LDPE film was washed with fresh toluene to remove surface catalyst residues. The Schlenk tube was then connected to a high vacuum line and the toluene was removed by pumping. Next, the film was allowed to contact acetylene gas (initial pressure ca. 700 torr) for various periods of time. Polymerizations were carried out at temperatures between −78° and 110° C. The high temperature polymerization was preferred since the polymerization rate is maximized without excessive melting of the matrix. During the high temperature polymerizations, the organge-brown catalyst impregnated LDPE film turned from blue to black as the acetylene diffuses into the film and polymerizes at the catalyst sites. Samples containing >ca. 5 wt. % $(CH)_x$ had a dull golden luster. The amount of $(CH)_x$ in the blends was determined and elemental analysis of the resulting materials, which typically contain ca. 0.15 wt. % and 0.20 wt. % of Ti and A1, respectively. The results from both methods were generally in good agreement.

(c) Solvent Blend - Polystyrene

A similar procedure was used, with some modification, to prepare polystyrene/$(CH)_x$ blends. Since polystyrene was soluble in the catalyst solution described above, impregnated films were prepared by evaporation of the solvent. After exposure to acetylene, black polystyrene/ $(CH)_x$ blends were obtained. Exposure to iodine vapor rendered the blends conductive in the range from about 10 $-^{10}$ to about 10$^{1}$ $^{-1}$ cm$^{-1}$. The blends soften above 100° C. depending on the blend composition.

EXAMPLE II

Doping of Polyacetylene Films (a) Film doping

A film of polyacetylene, (prepared as in Example 1, (a, b, or c) 10 cm diameter X 0.5 mm thick is doped to a nominal resistance of 1 megohm/cm using 50 mg of iodine dissolved in 100 ml of hexane by, bathing the film overnight at room temperature, followed by rinsing with hexane and then drying under vacuum.

(b) Contact preparation.

A thick film hybrid electrode pattern is applied to one side of the polyacetylene film by spraying, through a mask, a colloidal graphite paint, commercially available as Electrodag 114 or equivalent (Acheson Colloids, Lake Huron, MI). the pattern is arranged so that three or more electrode "regions" are defined by the thick film hybrid graphite paint, allowing for two or more regions across which the resistance of the semiconductive polyacetylene film can be measured simultaneously.

(c) Resistance determination.

The surface resistance is determined, using the ohmmeter setting and a two-points, probe fixture, with a Keithley Model 197 DMM Digital Multimeter (Keithley Instruments, 28775 Aurora Road, Cleveland, Ohio 44139). Resistance measurements with the Keithley are constant current with a maximum voltage across the unknown of 4.0 volts.

EXAMPLE III

Polyacetylene Electrode Cell

The iodine doped polyacetylene blend film is punched into disks of 9 mm diameter disks and electrodes provided on the reverse side in accordance with the procedure of Example IIb.

The electrodes are spaced as an isosceles triangle (for two electrode pairs comprised of three distinct electrode regions, with one electrode region common) and are aligned to contact with 2.2 mm diameter inconel pins similarly spaced in the lower portion of the Delrin assembly.

In order to make electrical measurements of the polyacetylene blend film while it is in contact with various aqueous solutions, a specially designed and fabricated electrode cell is used (FIG. 3). The cells are machined from Delrin, and incorporate a threaded nut to secure the electrodes to the bottom of the film (aligned with the respective colloidal graphite electrode patterns) away from the liquid in the sample well. The sample well can accommodate up to 500 ul of solution.

EXAMPLE IV

Figures 1, 6:
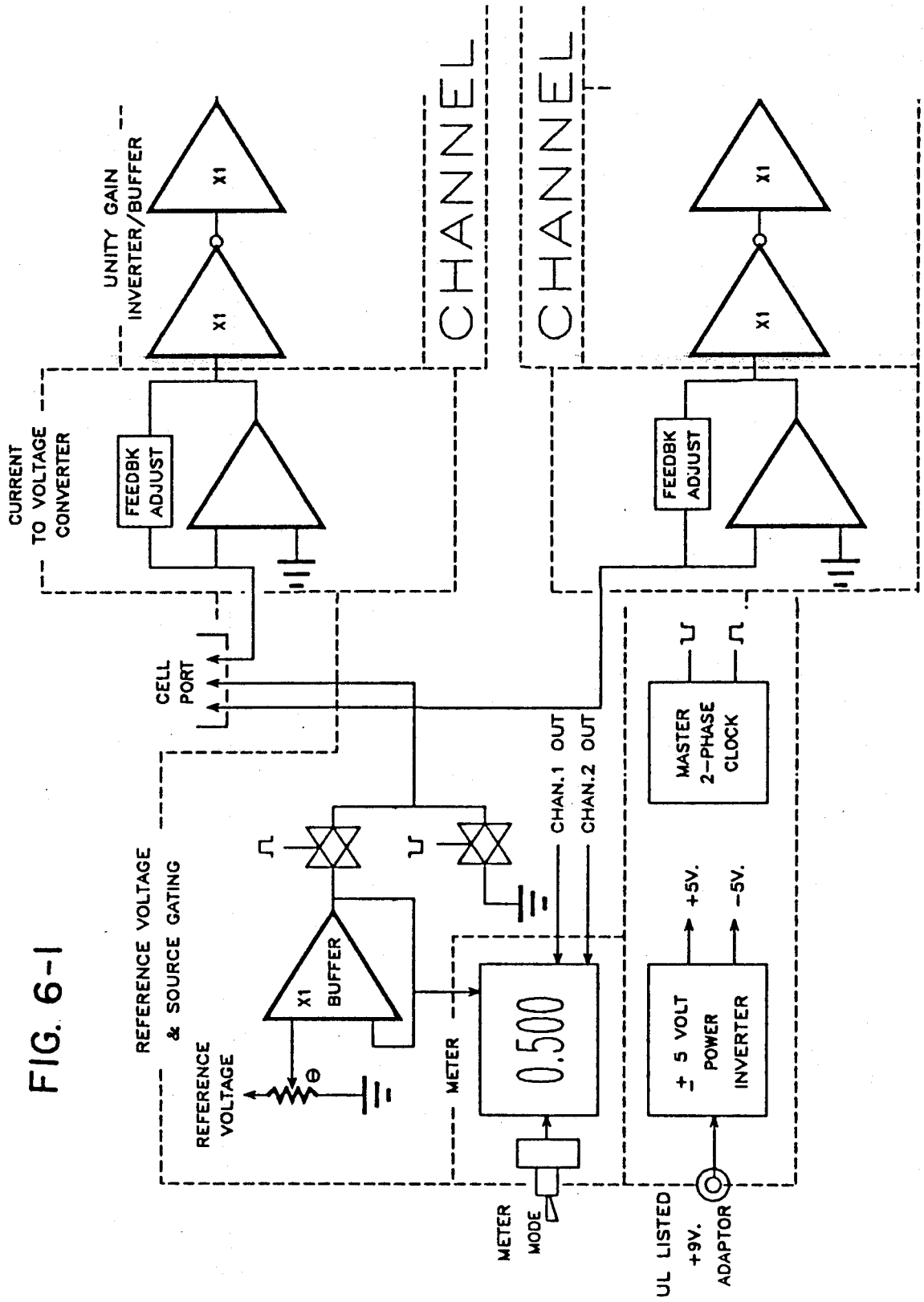
FIG. 6 is a circuit diagram of a detection system utilized in the present invention.
Figures 2, 6:
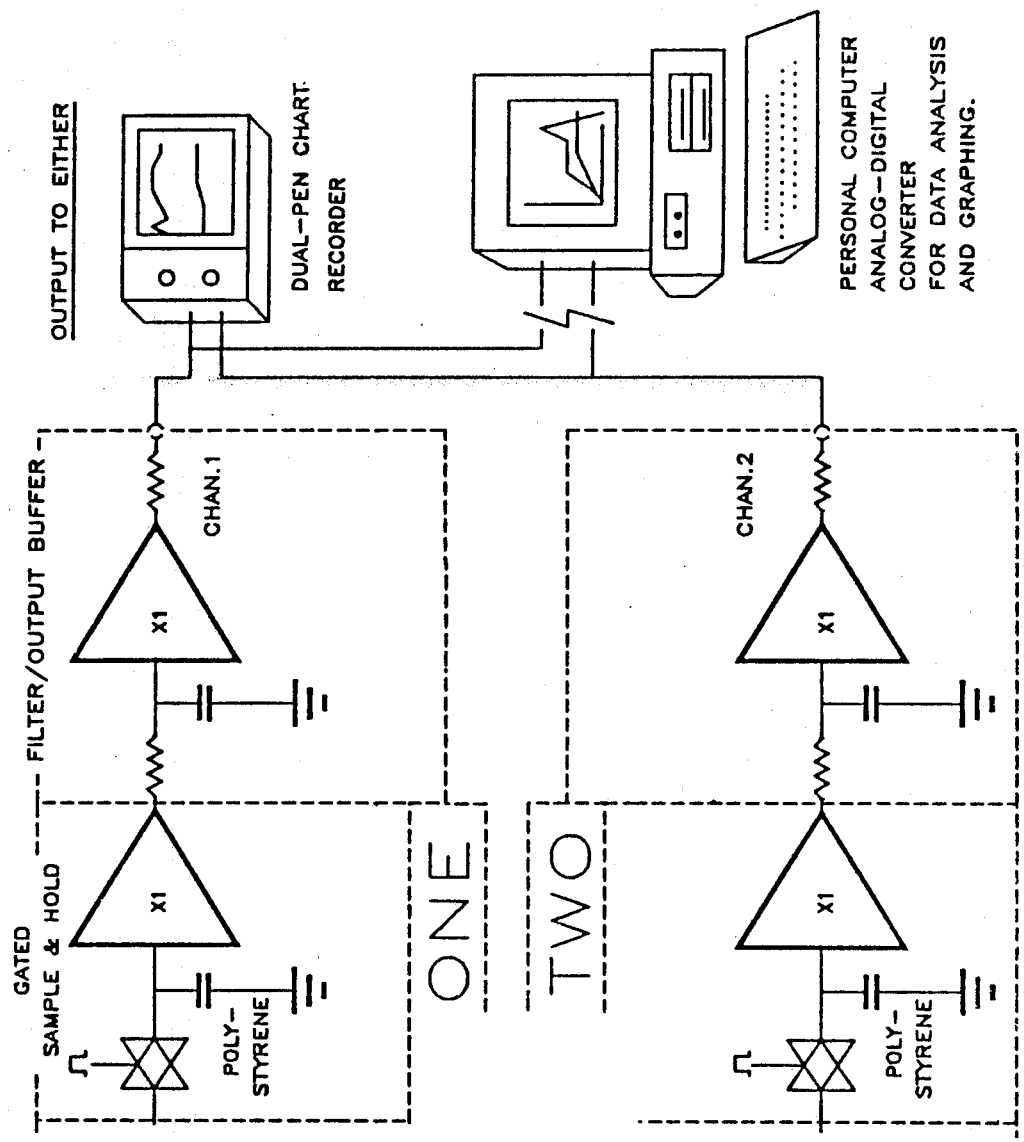
Figure 7:
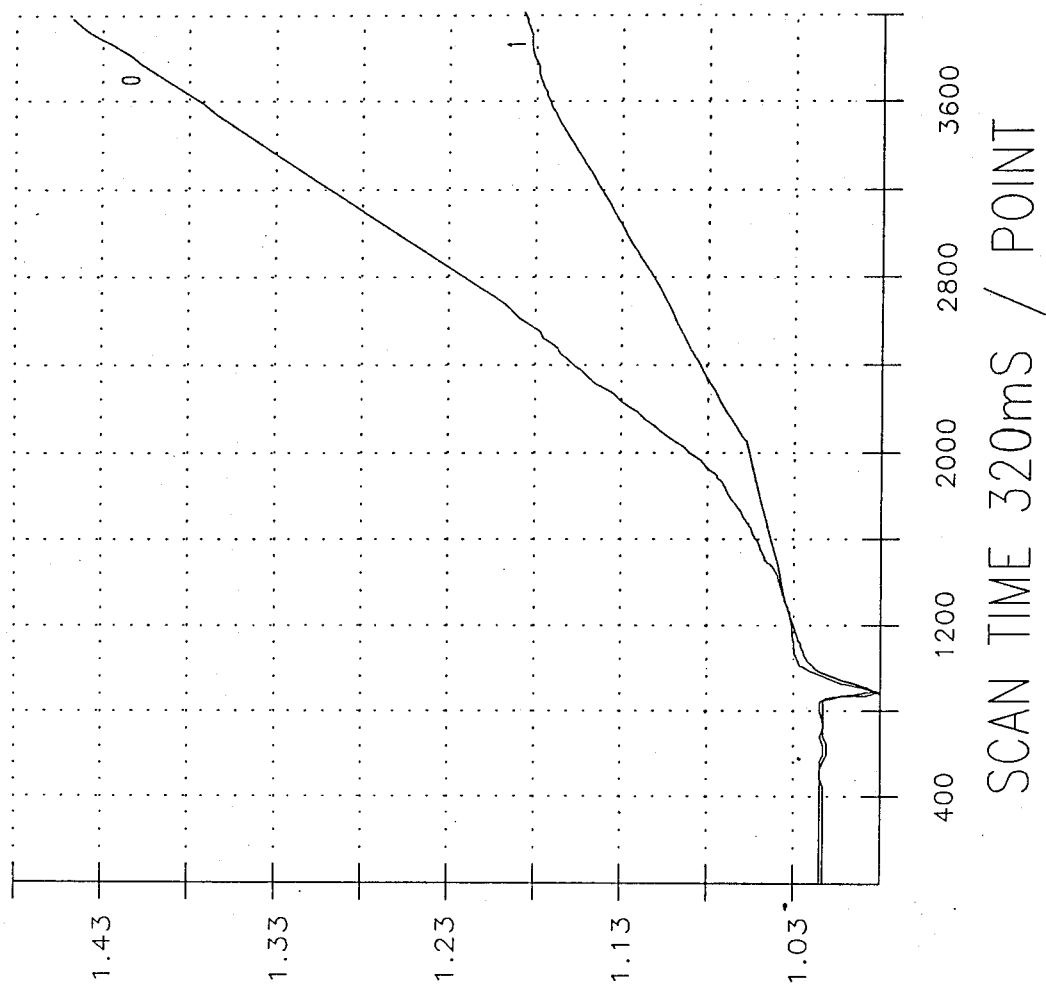
FIG. 7 is a graph showing analyte response and background in a particular test.

Instrumentation (FIG. 6)

Simple resistance measurements of dry samples of polyacetylene films mount in the electrode cell are made with the ohmmeter setting on the Keithley 197 DMM. When an aqueous electrolyte solution, such as a typical biological buffer (sodium phosphate buffer saline, for example) is added to the sample well above the polyacetylene film, the resistance measurements are complicated by a capacitive charge separation effect. To obtain precise, consistant resistance measurements of the hydrated polyacetylene films, a pulsed sample-and-hold amplifier is used, following an operational amplifier configured as a current-to-voltage converter. Nominally, a 500 mv potential is pulsed across the electrodes, using a 100 us or 0.1 mS "precise period" pulse, with a 10 mS repetition rate, for a duty cycle of 1%. The current is thus sampled at the end of the 100 uS pulse. Output from the filtered (low pass filter time constant of 100 milliseconds) sample-and-hold amplified is read into an IBM PC XT using a Data Translation A/D D/A Interface Board DT 2805. All data collection, analysis and plotting are supported using the ASYST Scientific Data Acquisition and Analysis Software (Macmillan Software). Each electrode pair on a single sample of the polyacetylene film is connected to a separate sample-and-hold amplified, providing a means to measure conductivity changes between each electrode pair across the corresponding region of the conductive polymer film, or to measure such changes differentially, where a change common to both electrode pairs is nulled out allowing only changes unique to one electrode pair region to be recorded.

EXAMPLE IV

A bi-molecular complex of the enzymes glucose oxidase and lactoperoxidase is prepared using p-benzoquinone following the basic procedure as described by Terynck and Averamean, Immunochemistry 14, 767–774 (1977).

Glucose oxidase (GOX, Sigma, Type VII) is dissolved in 0.15M NaCl at a concentration of 10 mg/ml and dialyzed overnight at 4° C. against 0.15M NaCl. 4 mg of the GOX solution in 0.4 ml are brought to pH 6.0 with the addition of 0.05 ml of 1M solution phosphate buffer at pH 6.0. 0.1 ml. of a freshly prepared p-benzoquinone solution in ethanol (30 mg/ml) is added, mixed and the solution kept for 1 hour at room temperature (less than 22° C.) in the dark.

The sample is filtered through a Sephadex G-25 fine column (0.9×4 cm; a 5 ml disposable glass syringe barrel is ideal), equilibrated with 0.15M NaCl. The first colored fraction eluted in about 1 ml volume is collected. Lactoperoxidase (Sigma, type ) 2 mg in 100 ul of solution previously dialyzed overnight against 0.15M NaCl, is added, generally to approximately 4 mg of GOX. One-tenth volume of a freshly prepared 1M $NaHCO_3$ solution is then added and the reaction mixture kept 48 hours at 4° C. One volume of a 1M lysine solution in PBS is added and after 4 hours at 4° C., the solution is dialyzed overnight against PBS. The solution is centrifuged at 7000 g and stored at 4° C.

EXAMPLE V

Sandwich Assay for "Avidin" (FIG. 5a)

The Delrin CPF cell is connected to the dual channel sample and hold amplifier the output of which is connected to a personal computer for data acquisition and subsequent analysis. The cell is pre-equilibrated with a volume (typically 200 ul) of a PBS pH 6.2 with 0.02M KI and 5 gm/100 ml of glucose,. The sample, containing analyte, in this example, avidin (ng/ml), in 100 ml is first added to the cell, immediately followed by a 100 ml of the biotinylated enzyme complex (B-GOX-LPO) (mg/ml) in a 1% BSA/PBS buffer with 1% glucose.

EXAMPLE VI

"Reverse" Sandwich Enzyme Imunoassay (FIG. 5b)

Iodine doped polyacetylene composite films (CPF), mounted in the Delrin electrode cell are coated with biotinylated lactoperoxidase (Sigma) by direct adsorption, using 1 ug/ml in PBS pH 7.2 overnight at room temperature, followed by washing at least 3 times with PBS. Using an insert which separates the Delrin electode cell into two compartments over the pair of electrode regions on the CPF, one side is coated with the biotinylated LPO (sample side), while the reference side is coated with underivatized LPO. After washing, the insert is removed.

Other methods may be employed for the differential coating of a specific binding macromolecule on the CPF element.

EXAMPLE VII

Competitive Homogeneous Assay for Secobarbitol (FIG. 5d)

As in Example V, a CPF element is mounted in the Delrin cell into which a split well insert (50) is carefully mounted. The film is coated on one side of the cell (sample side) with a concentration (typically 500 ng of total protein in 500 ul of PBS pH 7.2) of an antisecobarbital antibody conjugated to the enzyme lactoperoxidase by the procedure described in example IV. A comparable amount of lactoperoxidase (unconjugated) is similarly coated on the reference side of the cell. Both sides are coated for 3 to 16 hours, the insert removed and excess unbound protein washed out 3× with PBS pH 7.2.

The CPF sensor as prepared is connected to the dual channel sample and hold amplifier as previously described. A typical sample (urine, suspected of containing secobarbital at a concentration greater than 50 mg/ml) of 100 ul volume is added immediately followed by a 100 ul of solution containing an appropriate titlered concentration of a secobarbital-glucose to that described in Example IV.

An additional 100 ul of 1% glucose in a BSA-PBS-KI buffer pH 7.2 is subsequently added to the cell to intiate the kinetic enzyme response.

EXAMPLE VIII

Competitive Homogeneous Assay for Secobarbitol (FIG. 5d)

A preembodiment of the assay described in Example VII above can be made by coating the reference side of the cell with a conjugate of Lactoperoxidase and avidin along with the LPO-anti-secobarbital conjugate on the sample side. In this example, the secobarbital-complex conjugate is mixed with a titered concentration of a biotin-complex conjugate so that a comparable amount of binding of measurable complex activity will occur without any displacement by the secobarbital analyte. When a sample containing secobarbital is assayed, as previously described, the sample response will be measurably and proportionately lower than the reference side, providing a positive control against which the displaced response can be quantitatively measured.

EXAMPLE IX

Homogeneous Sandwich Assay for Salmonella Toxin (FIG. 5e)

Iodine doped polyacetylene blend films (CPF), mounted in Delrin electrode cells with the split well insert are coated on one side (sample side) with a specific lactoperoxidase-anti-Salmonella antibody (usually against the flagellar protein) conjugate. The reference side of the cell is similarly coated with a lactoperoxidase conjugated with a non-specific antibody. The insert is removed and the excess unadsorbed conjugates are washed from the cell.

The coated CPF cell is connected to the sample and hold amplifier as previously described. A sample of 100 ul volume, usually a culture broth suspected of containing Salmonella (at a concentration of $10^5$ cells/ml or greater) is acidified and re-neutralized to free the flagellar antigen, is added to the cell followed by a 100 ul volume of an anti-salmonella-antibody conjugate to the lactoperoxidase-glucose oxidase complex. The antibody for the complex conjugate may be of the same competitive epitope specificity or specific to a different epitope found on the flagellar antigen. At some interval of time later, the measurement is made by the addition of 100 ul of substrate solution containing 3% glucose in a BSA-PBS-KI buffer pH 7.2. The presence of specific Salmonella is made by a measurable response greater than any non-specific response observed from the reference side of the CPF cell.

In a similar fashion, the choice of macromolecular binding reactions that may be employed in the practice of this art, is not limited to specific antigen-antibody binding parts, but would include any complimentary macromolecular binding reaction pair that may be known or devised such as the specific hybridization of complimentary strands of polynucleic acids such as DNA or RNA, etc., or alternatively specific binding protein systems such as biotin-avidin, throxyanine and throxine binding globulin (TBG), riboflavin and riboflavin binding protect (RBP cortisol and cortisol binding protein (CBG), folate and folate binding protein (FBP) and related biomolecular protein binding systems that are generally known the field.

We claim:

1. A sensor means for conducting immunoassays comprising:
   a film of semiconductive polymer having an obverse and reverse surface,
   a common electroconductive area on the reverse surface in contact therewith,
   at least one further electroconductive area of the same electroconductive material as in said common area on said reverse surface and in contact therewith,
   at least one second further electroconductive area placed at a different location on the reverse surface and in contact therewith,
   means for separating the obverse surface of the film in such a manner that the a first field is defined over said first electroconductive area and a second field is defined over said second electroconductive area while a portion of each of said fields lies over the said common electroconductive area.

2. A sensor means of claim 1 wherein the said first and second electroconductive areas are equidistant from the common area.

3. A sensor means of claim 1 wherein the said first and second electroconductive areas are equal in area.

4. A sensor means of claim 1 comprising:
   a film of semiconductive polymer having an obverse and reverse surface,
   a narrow electroconductive strip on the reverse surface in contact therewith, said strip dividing said film into two fields of equal area,
   at least one further electroconductive area of the same electroconductive material as the said strip placed on said reverse surface and in contact therewith, on one field,
   at least one second further electroconductive area placed on the remaining field on the reverse surface and in contact therewith in such a manner that the electroconductive areas on both fields are equally large and equidistant from the said strip.

5. A sensor means of claim 4 wherein the separating means on the obverse side of the film is
   a masking layer of non conductive material placed on and in contact with the obverse surface of a film to provide unmasked areas of equal size on either side of the longitudinal axis of said strip and lying over at least an equal portion of that area occupied by each of said first and said second electroconductive areas in the fields on the reverse side of the film and over at least a portion of said strip.

6. A sensor means of claim 4 wherein the film is substantially circular and the first and second electroconductive areas are defined by the areas between the circumference of the circle and chords spaced apart from and at an equal inclination to the diameter which constitutes the longitudinal axis of said electroconductive strip.

7. An immunoassay sensor cell comprising a sensor means of claim 1, electrical connection means to said electroconductive areas, a sample reservoir having an open upper and lower end, the portion of said reservoir surrounding said open lower end being adapted to contact and form a liquid leakproof seal with the obverse surface of the film, of sufficient size to encompass at least the obverse surface over the electroconductive areas on the reverse side, a dual chamber insert, adapted to fit removably inside said reservoir, having open upper and lower ends, the portion of said insert surrounding said open lower end being adapted to contact and form a liquid leakproof seal with the obverse surface of the film and being of sufficient size to encompass at least a part of the obverse surface over the electroconductive areas on the reverse side within said open lower end and having a center partition similarly adapted to contact and form a liquid leakproof seal with the obverse surface of the film.

8. A device of claim 7 wherein the common electroconductive area is a narrow electroconductive strip on the reverse surface in contact therewith, said strip dividing said film into two fields of equal area, and the first and second other electroconductive areas are at least one further electroconductive area of the same electroconductive material as the said strip placed on said reverse surface and in contact therewith, on one field, and at least one second further electroconductive area placed on the remaining field on the reverse surface and in contact therewith in such a manner that the electroconductive areas on both fields are equally large and equidistant from the said strip, whereby said central partition defines two fields of equal area on either side of the longitudinal axis of the said strip, upon the obverse side of the film.

* * * * *